United States Patent [19]
Uchida et al.

[11] Patent Number: 5,538,947
[45] Date of Patent: * Jul. 23, 1996

[54] GROWTH INHIBITORY FACTOR

[75] Inventors: Yoko Uchida, Tokyo; Yasuo Ihara, Yokohama, both of Japan

[73] Assignee: Takeda Chemical Industries, Ltd., Japan

[*] Notice: The term of this patent shall not extend beyond the expiration date of Pat. No. 5,214,031.

[21] Appl. No.: 138,340

[22] Filed: Oct. 18, 1993

[30] Foreign Application Priority Data

Oct. 19, 1992 [JP] Japan .................. 4-280201
Dec. 25, 1992 [JP] Japan .................. 4-346853

[51] Int. Cl.⁶ .................. A61K 38/10; C07K 7/08; C07K 14/00
[52] U.S. Cl. .................. 514/12; 514/13; 514/2; 530/324; 530/325; 530/317; 530/326
[58] Field of Search .................. 530/324, 317, 530/325, 326, 399; 514/12, 13, 2

[56] References Cited

U.S. PATENT DOCUMENTS 5,077,276  12/1991  Ballard et al. .................. 514/12
5,214,031  5/1993   Uchida .................. 514/12

FOREIGN PATENT DOCUMENTS 0458673    11/1991  European Pat. Off..
W092/10568 12/1990  WIPO.

OTHER PUBLICATIONS

The Merck Manual of Diagnosis & Therapy, pp. 1161–1163, 11th ed., (1966).
Callegaro et al, Chem. Abs., vol. 119, (153,373), 1993.
Brain Research, vol. 481, pp. 190–193 (1989), Uchida et al. "Neurotrophic Action . . . Neurons".
Biochemical and Biophysical Research Communication, vol. 150(3), pp. 1263–1267 (1988); Uchida, et al, "Alzheimier's . . . Rats".

*Primary Examiner*—Jill Warden
*Assistant Examiner*—T. D. Wessendorf
*Attorney, Agent, or Firm*—Bierman and Muserlian

[57] ABSTRACT

Disclosed is a non-naturally-occurring polypeptide having neural growth inhibitory action which has an amino acid sequence represented by the formula:

Thr Cys Pro Cys Pro Ser Gly Gly Ser Cys Thr Cys Ala Asp Ser Cys Lys Cys Glu.

The polypeptide of the present invention having neural growth inhibitory action is useful for the treatment of Alzheimer's disease.

5 Claims, 6 Drawing Sheets

GROWTH INHIBITORY FACTOR

BACKGROUND OF THE INVENTION

The present invention relates to a polypeptide having neural growth inhibitory action.

Amidst the growing number of elderly people in our society, the issue of senile dementia is attracting considerable concern, and numerous efforts have been made for its prevention and treatment. In particular, since a senile dementia known as Alzheimer's disease frequently occurs in presenium (age 50–60), elucidation of its cause and establishment of a method of treatment are greatly desired.

According to findings obtained thus far, Alzheimer's disease is considered to be an organic disease having both pathological characteristics such as senile plaques and neurofibrillary degeneration, as well as clinical characteristics such as progressive dementia. In addition, acceleration metabolism and abnormal regeneration of neuron are involved in this disease.

A novel protein having neural growth inhibitory action (growth inhibitory factor, GIF) was separated and found during the course of research on the brain components of Alzheimer's patients, which exists in the brains of normal persons but disappears from the brains of Alzheimer's patients, along with a process for producing said GIF using genetic engineering techniques, were respectively disclosed in Japanese Provisional Unexamined Patent Application (KOKAI) No. 18100/1992, European Unexamined Patent Application No. 458,673 and PCT Patent Publication No. WO92/10568.

Since it would be possible to study the GIF action if detailed information were obtained concerning its active site, the potential for use as a pharmaceutical drug would be greatly increased.

In addition, if it is possible to use a smaller polypeptide containing the active site as a pharmaceutical drug, it would be more advantageous in terms of production and preparation as a pharmaceutical preparation.

SUMMARY OF THE INVENTION

While the present inventors studied the activity of GIF using its fragments for the purpose of determining its mechanism of action, it was discovered that a polypeptide containing an amino acid sequence of the 5th to 23rd amino acid residues from the N terminal of GIF demonstrates excellent GIF activity. Further research based on this findings then resulted in completion of the present invention.

An object of the present invention is to provide a non-naturally-occurring polypeptide having neural growth inhibitory action that contains the amino acid sequence represented by the following amino acid sequence (I):

Thr Cys Pro Cys Pro Ser Gly Gly Ser Cys Thr Cys Ala Asp Ser
      Cys Lys Cys Glu (I)                    (SEQ ID No. 1)

DESCRIPTION OF THE PREFERRED EMBODIMENTS

Figure 1:
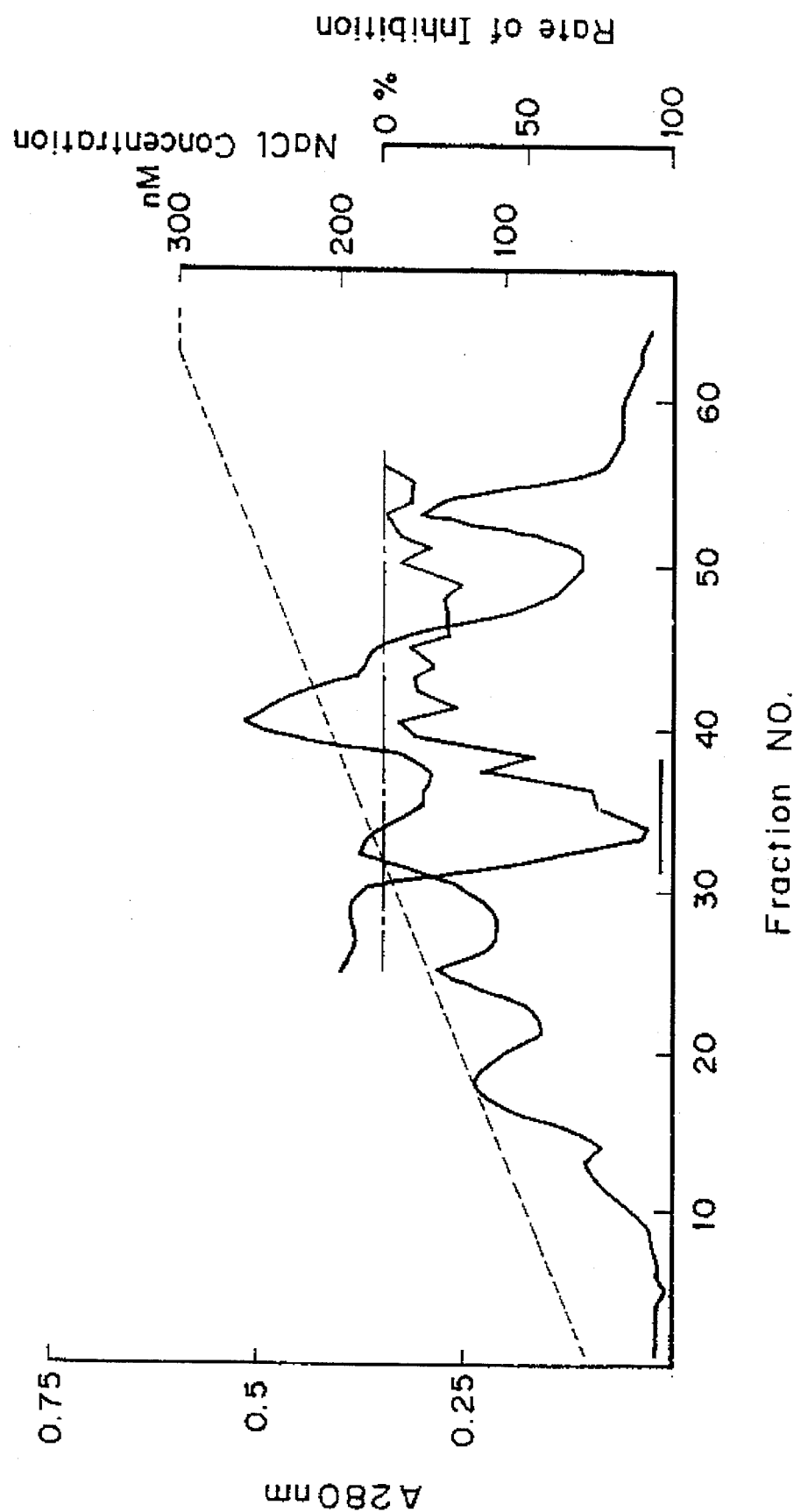
FIG. 1 shows a chromatogram resulting from homogenizing normal human cerebral cortex, performing ultrafiltration, and applying the fraction having a molecular weight of 10 kilodaltons or more to a DEAE-Sephacel column.

The polypeptide of the present invention is a non-naturally-occurring peptide containing the amino acid sequence represented by SEQ ID No. 1. Thus, the above-mentioned naturally-occurring GIF is excluded.

Examples of the polypeptide of the present invention include the polypeptide having the amino acid sequence represented by SEQ ID No. 1, as well as a polypeptide which may contain the amino acid sequence and in which amino acid(s) are linked to its N terminal and/or C terminal as long as neural growth inhibitory action is exhibited. Further, the polypeptide of the present invention may have at least one disulfide linkage.

The number of amino acids which are linked is, for example, 1–10, preferably 1–5, and more preferably 1–3. Specific examples of said linked amino acids include one or more of methionine, tyrosine, serine and threonine as an example or examples of amino acids linked to the N terminal, and one or more of tyrosine, serine and threonine as examples of amino acids linked to the C terminal.

The polypeptide of the present invention can be produced by performing a peptide chain cleaving reaction on the GIF prepared by the process described in, for example, Japanese Provisional Unexamined Patent Application (KOKAI) No. 18100/1992, European Unexamined Patent Application No. 458,673 or PCT Patent Publication WO92/10568.

For example, said cleaving reaction can be carried out by using a digestion enzyme on said GIF.

An example of said enzyme is a protease which may be either an exopeptidase or endopeptidase.

Examples of said proteases include serine proteases (e.g. trypsin, chymotrypsin, thrombin, plasmin, elastase and V8), thiol proteases (e.g. cysteine protease, papain, ficin, bromelain and cathepsin B), acidic proteases (e.g. aspartate protease, pepsin, cathepsin D, renin and chymosin), and metal proteases (e.g. carboxyprotease, collagenase and thermolysin).

In particular, endopeptidases (e.g. trypsin, V8 and metal proteases) are used preferably.

Said enzyme reaction is carried out by reacting a purified or partially purified product of GIF with an enzyme as mentioned above.

Said reaction is preferably carried out using a buffer solution. Examples of said buffer solution include those composed of salts of an inorganic acid (such as phosphoric acid) or organic acid (such as acetic acid) and an inorganic base (such as sodium hydroxide, potassium hydroxide or ammonia). Any of said buffer solutions may be used as long as it does not inhibit said enzyme reaction.

The pH of said enzyme reaction is in the range of approximately 2–10, preferably approximately 6–9 in terms of stability of the enzyme and polypeptide. The reaction time may preferably be in the range of approximately 1–100 hours, and most preferably of approximately 18–24 hours. The reaction temperature is approximately 4°–70° C., while that of between approximately 20°–37° C. is particularly preferable. The amount of a peptidase used in the reaction should be approximately 1/1000–1 (mole ratio) with respect to the amount of a substrate, namely GIF, and an amount of approximately 1/300–1/20 (mole ratio) is preferable in terms of yield, reaction time and economic feasibility.

During said enzyme reaction, an aminopeptidase can be used in the reaction after fixing on agarose, dextran, cellulose, polyacrylamide, their derivatives or their copolymers.

In addition, methionine in the sequence consisting of Met-Asp-Pro may be cleaved specifically with the action of an aminopeptidase. Said process is performed according to the process described in European Unexamined Patent Application No. 204,527.

In addition, the polypeptide of the present invention can also be produced using a synthesis process.

Chemical synthesis of the polypeptide of the present invention can be performed using an automated peptide synthesizer. The basic synthesis process and so forth can be performed following the method of R. B. Merrifield [Advances in Enzymology, 32, 221–296 (1969)]. The principle of this method involves covalently bonding the amino acid of the carboxyl terminal to a resin support, removing the protecting group of the α-amino group, sequentially repeating condensation of protected amino acids and extending the peptide chain towards the amino terminal to obtain a protected peptide resin having the target amino acid sequence. Since condensation of each amino acid and removal of the protecting group of the α-amino acid group are performed under nearly identical conditions and purification of intermediates is not carried out, this synthesis does not generally require advanced skills. Moreover, this method can be performed quickly and is extremely useful for synthesizing various peptides. By then allowing the resulting protected peptide resin to react in the presence of, for example, anhydrous hydrogen fluoride, trifluoromethanesulfonic acid or trifluoroacetic acid and various additives, dissociation of the peptide from the resin and removal of all protecting groups can be performed in a single step.

Isolation and purification of the target peptide should be performed according to routine known methods for peptide purification. This can be performed by suitably combining such purification methods as gel filtration, ion exchange chromatography, high-performance liquid chromatography, affinity chromatography, hydrophobic chromatography, thin layer chromatography and electrophoresis.

The polypeptide of the present invention obtained in this manner having neural growth inhibitory action is useful as a pharmaceutical drug for treatment of Alzheimer's disease. In addition, said polypeptide has lower toxicity.

When using the polypeptide of the present invention having neural growth inhibitory action as a pharmaceutical drug, it can be administered safely to warm-blooded animals (including humans, mice, rats, hamsters, rabbits, dogs and cats), either parenterally or orally, in its original form as a powder or as a pharmaceutical composition (e.g. injection preparation, tablets, capsules, liquid or ointment) together with other pharmacologically acceptable carriers, vehicles and diluents.

The production of an injection preparation is performed according to conventional methods using an aqueous solution containing, for example, physiological saline or glucose and other adjuvants. Pharmaceutical compositions such as tablets and capsules can also be prepared according to conventional methods.

In the case of using the polypeptide of the present invention having neural growth inhibitory action as a pharmaceutical drug, it is administered, for example, to the warm-blooded animals listed above by selecting a suitable dose from approximately 1 ng/kg per day to 1 mg/kg per day in consideration of administration route, symptoms and so forth.

The abbreviations of amino acids, peptides, protecting groups, active groups and so forth used in this specification are either abbreviations in accordance with IUPAC-IUB (Commission on Biochemical Nomenclature) or commonly used abbreviations in the art. Examples are indicated below. In addition, when amino acids are capable of existing as optical isomers, those isomers mean the L form unless indicated otherwise.

A, Ala: Alanine
C, Cys: Cysteine
D, Asp: Aspartic acid
E, Glu: Glutamic acid
F, Phe: Phenylalanine
G, Gly: Glycine
H, His: Histidine
I, Ile: Isoleucine
K, Lys: Lysine
L, Leu: Leucine
M, Met: Methionine
N, Asn: Asparagine
P, Pro: Proline
Q, Gln: Glutamine
R, Arg: Arginine
S, Ser: Serine
T, Thr: Threonine
V, Val: Valine
W, Trp: Tryptophan
Y, Tyr: Tyrosine

REFERENCE EXAMPLE 1

Separation and Purification of GIF

GIF was produced using the method described in Japanese Provisional Unexamined Patent Application No. 18100/1992 and its corresponding EP Application No. 458,673. Namely, 60 ml of water were added to 20 g of normal human cerebral cortex protein followed by homogenizing and centrifuging for 1 hour at 20,000 g to obtain 55 ml of supernatant.

Figure 2:
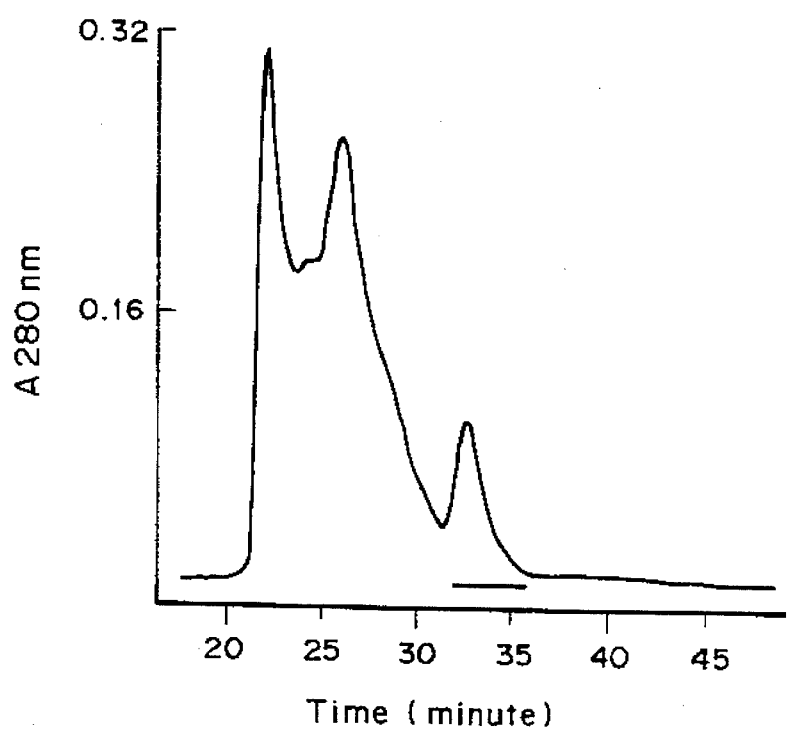
FIG. 2 shows a chromatogram resulting from performing gel filtration on a fraction having inhibitory activity during the course of purification of GIF.
Figure 3:
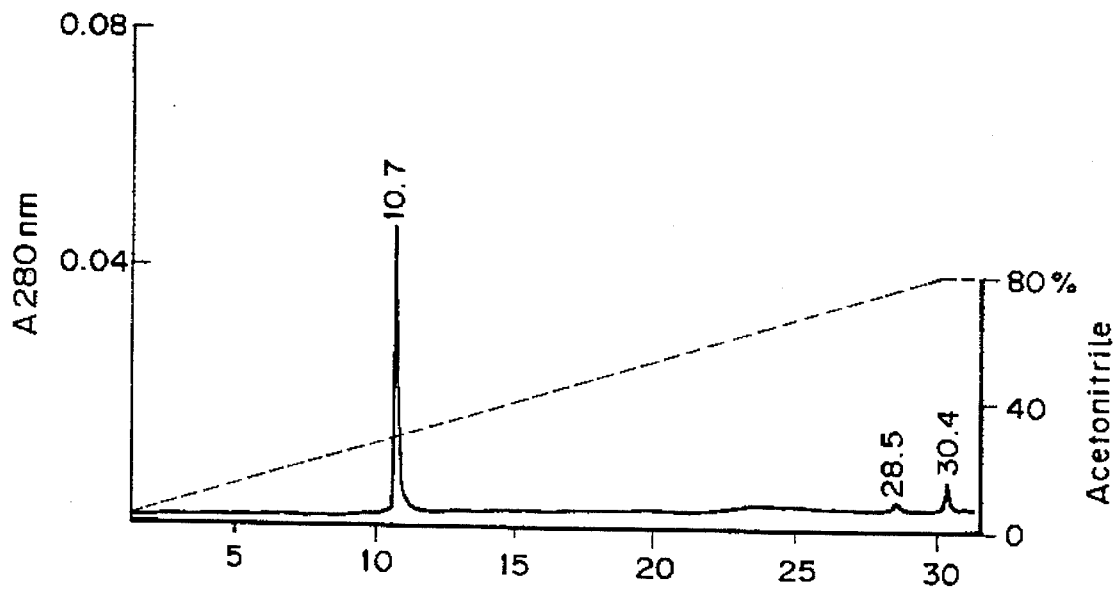
FIG. 3 shows a chromatogram resulting from applying GIF to C18 reverse-phase HPLC.

Ultrafiltration was performed on 55 ml of the resulting supernatant using the Amicon YM-10 membrane (Trade name), and a fraction containing components having a molecular weight of 10 kilodaltons or more was placed on a DEAE-Sephacel column (1.6 cm diameter×16 cm, Pharmacia). After washing with 200 ml of 50 mM NaCl containing 50 mM Tris-Cl buffer solution (pH 7.6), extraction was performed with 320 ml of 20 mM Tris-Cl (pH 7.6) buffer solution applying a linear concentration gradient from 50 mM to 300 mM NaCl. The chromatogram thus obtained from the DEAE-Sephacel column is shown in FIG. 1. Fractions from no. 31 to no. 38 having neural growth inhibitory activity were collected (40 ml). After concentration using Ficoll 400 following dialysis, gel filtration (column size: 7.5 mm diameter×6 cm) was performed with the TSK G2000 SW (Tosoh). Fraction nos. 30 to 32 were collected (2.5 ml) and dialyzed in a 5 mM phosphate buffer (pH 7.4). The results of gel filtration chromatography using the TSK G2000 SW are shown in FIG. 2. After concentrating to a liquid volume of 550 µl, the liquid was applied to a C18 reverse phase HPLC column (4.6 mm diameter×25 cm, Senshu Chemical). An aqueous solution of a 5 mM ammonium formate applying a linear concentration gradient of 0–80% acetonitrile was used for elution. The results of this C18 reverse-phase HPLC chromatography are shown in FIG. 3. As shown in FIG. 3, a single sharp peak was obtained by C18 reverse-phase HPLC chromatography, thus indicating isolation of GIF.

EXAMPLE 1

Digestion of GIF by Protease

Figure 4:
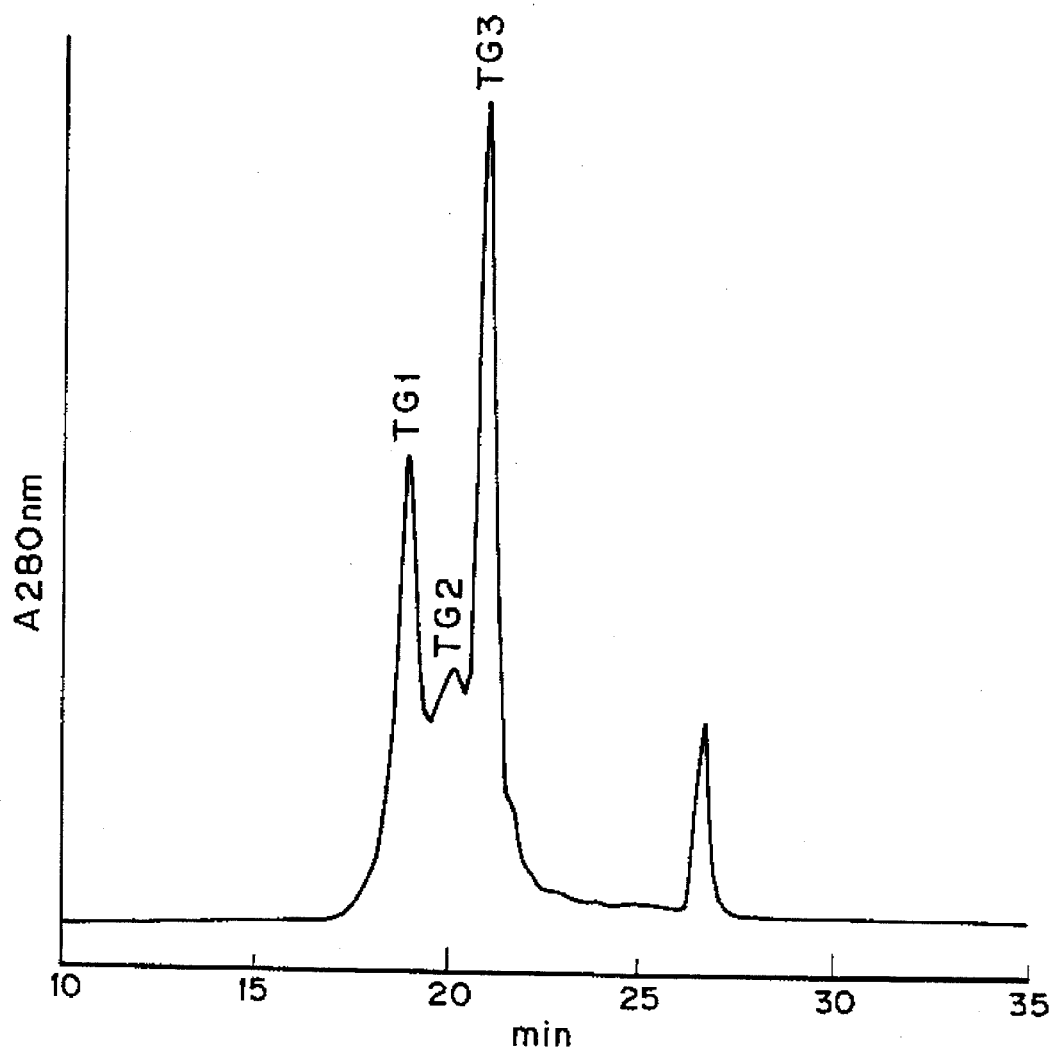
FIG. 4 shows a separation pattern resulting from column chromatography performed on the enzyme reaction products (trypsin digested product) obtained in Example 1.
Figure 5:
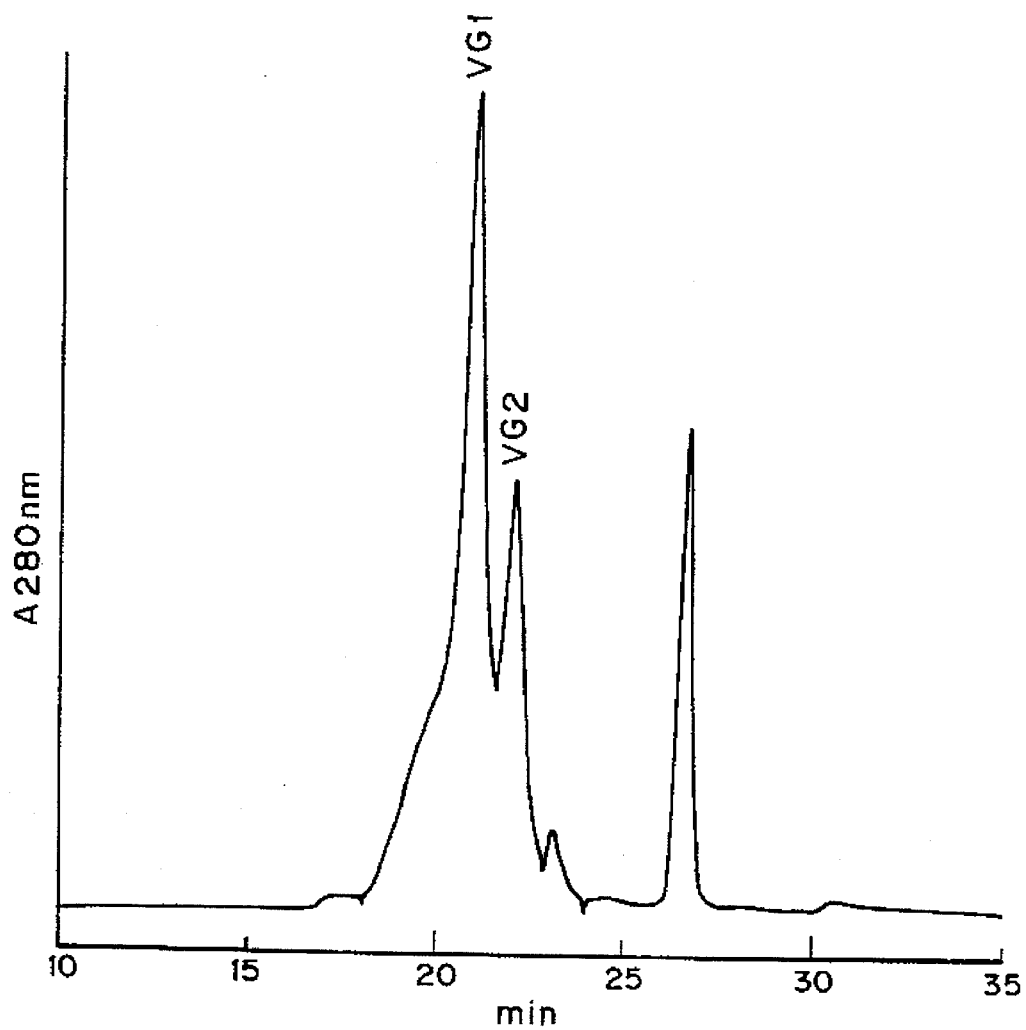
FIG. 5 shows a chromatogram from gel filtration column chromatography performed on the enzyme reaction products (V8 protease digested product) obtained in Example 1.

Fifty (50) µg of the GIF obtained in Reference Example 1 were pyridylethylated according to conventional methods. To thus obtained product was added 100 µl of an aqueous solution of 0.1M Tris-Cl (pH 8.0) containing 0.5 µg of trypsin (Sigma) and reacted for 18 hours at room temperature. The reaction product was separated with a GFA 30 gel filtration column. The separation pattern resulting from GFA 30 column chromatography is shown in FIG. 4. As shown in FIG. 4, three peaks (TG1, TG2 and TG3) were obtained. The fraction giving the peak TG3 product was collected, followed by digestion with V8 protease. The reaction product was separated with a GFA 30 gel filtration column. As a result, two peaks (VG1 and VG2) were obtained (FIG. 5). On the other hand, 400 µg of GIF obtained in Reference Example 1 were dissolved into 100 µl of a phosphaste buffer saline solution of Dulbecco and 0.5 mg of trypsin (Sigma) were added thereto. The obtained mixture was subjected to the same treatment as in the above to obtain the same digested product as in the above.

EXAMPLE 2

Amino Acid Sequence Analysis

Each of five digestion products obtained in Example 1 (TG1, TG2, TG3, VG1 and VG2) was fractionated and applied to a gas phase protein sequencer (Model 477A; Applied Biosystems) to determine the amino acid sequences of each peptide. As a result, each peptide was determined to have the amino acid sequences shown below.

```
GIF: MDPETCPCPS GGSCTCADSC KCEGCKCTSC
     KKSCCSCCPA ECEKCAKDCV CKGGEAAEAE AEKC-
     SCCQ                            (SEQ ID No. 2)

TG1: MDPETCPCPS GGSCTCADSC KCEGCKCTSC
     KKSCCSCCPA ECEKCAKDCV CKGGEAAEAE AEKC-
     SCCQ                            (SEQ ID No. 2)

TG2: MDPETCPCPS GGSCTCADSC KCEGCKCTSC
     KKSCCSCCPA ECEKCAKDCV CKGGEAAEAE AEKC-
     SCCQ                            (SEQ ID NO. 2)

TG3: MDPETCPCPS GGSCTCADSC KCEGCK  (SEQ ID No. 3)

VG1: MDPETCPCPS GGSCTCADSC KCEGCK  (SEQ ID No. 3)

VG2: TCPCPSGGSC TCADSCKCE         (SEQ ID No. 1)
```

EXAMPLE 3

Digestion of GIF by Protease

Two hundreds (200) µg of the GIF obtained in Reference Example 1 were dissolved in 200 ml of a phosphate buffered saline solution of Dulbecco. Thirteen (13) µg of trypsin (Sigma) were added thereto an incubated for 18 hours at room temperature. The reaction product was separated with a GFA 30 gel filtration column. The separation pattern resulting from GFA 30 column chromatography is shown in FIG. 4. As shown in FIG. 4, three peaks (TG1, TG2 and TG3) were obtained. The fraction giving the peak TG3 product was collected, followed by digestion with V8 protease. The reaction product was separated with a GFA 30 gel filtration column. As a result, two peaks (VG1 and VG2) were obtained (FIG. 5).

EXAMPLE 4

Amino Acid Sequence Analysis

Each of five digestion products obtained in Example 1 (TG1, TG2, TG3, VG1 and VG2) was digested with cyanogen bromide and oxidized with performic acid according to conventional methods. N-terminal sequence analyses were carried out on a PSQ-1 Protein Sequencer (Shimazu). Amino acid compositions were analyzed by JLC-300 Amino Acid Analyzer (JEOL) after hydrolysis with 6 NHCl. As a result, each peptide was determined to have the amino acid sequences shown below.

EXAMPLE 5

Assay of Neural Growth Inhibitory Activity $1.7 \times 10^4$ cells prepared from cerebral cortices of neonatal rats were seeded in a 6 mm microplate coated with gelatin-polyornithine. Each of the peptides obtained in Example 1 was added to serum-free medium MEMN2 (prepared by adding insulin, transferrin, putrescine, progesterone and sodium selenite to Eagle's medium) containing 100 µl of an aqueous solution of 125 µg/ml of Alzheimer's disease brain extract and fed for 5 days at 37° C. in a 5% carbon dioxide gas incubator. After fixing with para-formaldehyde and a solution of 90% methanol and 5% acetic acid, the amount of microtubule-bound protein 2 (MAP2: a protein specifically produced by neural cells) was determined by ELISA using anti-MAP2 antibody (Amersham). On the other hand, as control experiment, the amount of MAP2 was determined in the cultured cells only with Alzheimer's disease brain extract. Inhibitory activity was expressed by the percentage reduction rate (%) of the amount of MAP2.

Figure 6:
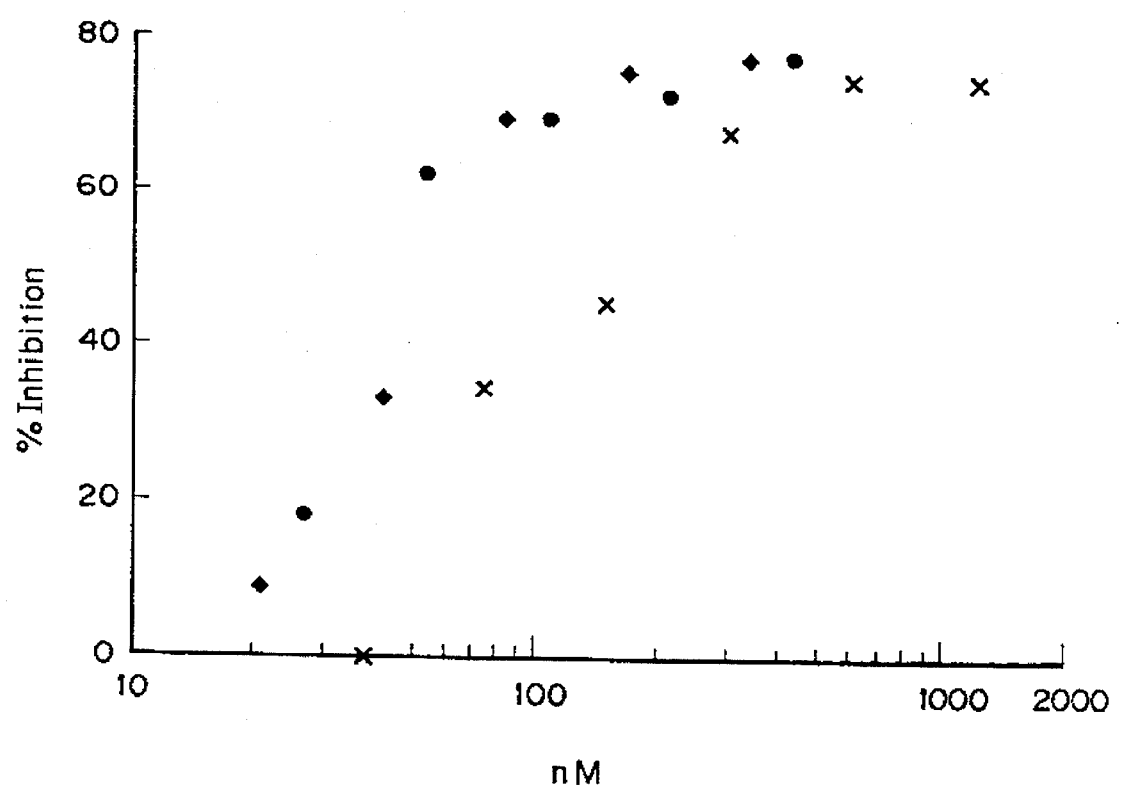
FIG. 6 is a graph that shows the neural growth inhibitory action of GIF and the polypeptide of the present invention measured in Example 3.

The relationship between the amount of peptide TG3 and VG2 and the percent inhibition of neural growth activity was determined using the method described above. Those results are shown in FIG. 6. In FIG. 6, the closed circle represents the results for GIF, the closed rhombus represents the results for TG3, and the x s represent the results for VG2. As shown in FIG. 6, both TG3 and VG2 clearly demonstrated neural growth inhibitory activity.

EXAMPLE 6

The following experiments were performed by using trypsin-digested TG3 (GIF1-26) which has growth inhibitory activity as intact GIF does.

Figure 7:
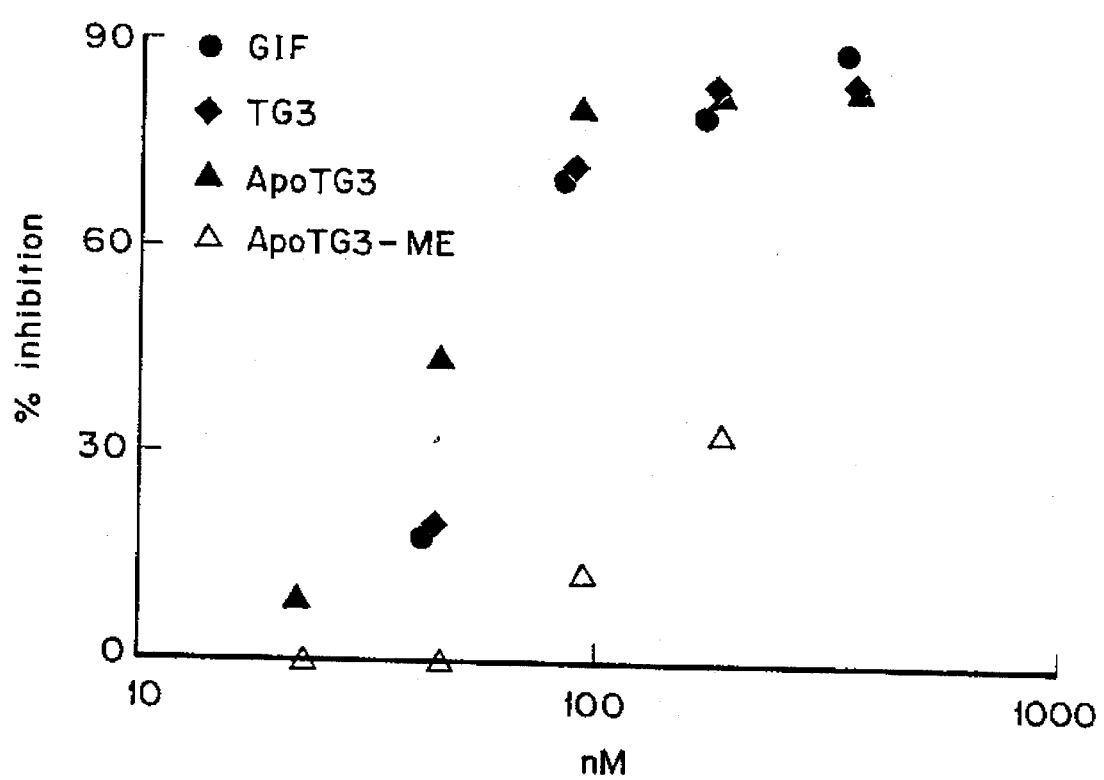
FIG. 7 is a graph that shows the neural growth inhibitory action of GIF and the polypeptide of the present invention measured in Example 6.

Metals were removed from TG3 by 0.1N HCl treatment, and ApoTG3 was separated by gel filtration with a GFA-30 column equilibrated with 0.01N HCl. This ApoTG3 had growth inhibitory activities. ApoTG3 was dissolved in PBS containing 2% β-mercaptoethanol and then β-mercaptoethanol was removed by gel filtration. This product, ApoTG3+ ME, did not have growth inhibitory activities. The result is shown in FIG. 7.

These experiments indicate that TG3 and ApoTG3, but not ApoTG3+ME have growth inhibitory activities although all 3 fragments have the same amino acid sequences. ApoTG3+ME is treated with mercaptoethanol and their S—S bonds are cut once and re-bound by auto-oxidation. Mercaptoethanol treatment changes the protein folding pattern of ApoTG3+ME to different pattern with TG3. In contrast, S—S bonds in ApoTG3 does not cut and the protein folding pattern of this peptide may not change with the protein folding pattern of TG3, in which S-metal bonds assign to.

The polypeptide of the present invention can be used for the treatment of Alzheimer's disease as a growth inhibitory factor. These growth inhibitory factors can be produced more easily than naturally-occurring polypeptide by genetic recombination technology or chemical synthesis. In addition, the factor of the present invention can also be administered more easily. Namely, as the polypeptide of the present invention is soluble in water, it can be easily made into a pharmaceutical preparation and is easily absorbed in the body. Since it is considered that the present peptide more easily pass through the brain barrier in view of its molecural size, as compared with a naturally-occuring GIF. Moreover, based on structural analysis of the factor of the present invention, it can also be used as a starting material for synthesizing compounds having similar action.

---

We claim:

1. A non-naturally-occurring polypeptide having neural growth inhibitory action consisting of the amino acid sequence represented by the formula:

Thr Cys Pro Cys Pro Ser Gly Gly Ser Cys Thr Cys Ala Asp Ser Cys Lys Cys Glu (SEQ ID NO:1).

2. A non-naturally-occurring polypeptide having neural growth inhibitory action consisting of the amino acid sequence represented by the formula:

Met Asp Pro Glu Thr Cys Pro Cys Pro Ser Gly Gly Ser Cys Thr
 1               5                10                    15

Cys Ala Asp Ser Cys Lys Cys Glu Gly Cys Lys (SEQ ID NO: 3).
         20                  25

3. A method of inducing growth-inhibiting activity in a human in need thereof comprising administering to said human being a neurotrophically inhibiting effective amount of the polypeptide of claim 1.

4. The polypeptide according to claim 1, which has at least one disulfide linkage.

5. The polypeptide according to claim 2, which has at least one disulfide linkage.

* * * * *

SEQUENCE LISTING ( 1 ) GENERAL INFORMATION:

( i i i ) NUMBER OF SEQUENCES: 3

( 2 ) INFORMATION FOR SEQ ID NO: 1:

( i ) SEQUENCE CHARACTERISTICS:
( A ) LENGTH: 19
( B ) TYPE: Amino Acid
( C ) STRANDEDNESS: Unknown
( D ) TOPOLOGY: Linear ( i i ) MOLECULE TYPE: Peptide ( x i ) SEQUENCE DESCRIPTION: SEQ ID NO:1:

Thr Cys Pro Cys Pro Ser Gly Gly Ser Cys Thr Cys Ala
1               5                       10

Asp Ser Cys Lys Cys Glu
        15

( 2 ) INFORMATION FOR SEQ ID NO: 2:

( i ) SEQUENCE CHARACTERISTICS:
( A ) LENGTH: 68
( B ) TYPE: Amino Acid
( C ) STRANDEDNESS: Unknown
( D ) TOPOLOGY: Linear ( i i ) MOLECULE TYPE: Peptide ( x i ) SEQUENCE DESCRIPTION: SEQ ID NO:2:

Met Asp Pro Glu Thr Cys Pro Cys Pro Ser Gly Gly Ser
1               5                   10

Cys Thr Cys Ala Asp Ser Cys Lys Cys Glu Gly Cys Lys
        15                  20                  25

Cys Thr Ser Cys Lys Lys Ser Cys Cys Ser Cys Cys Pro
                30              35

Ala Glu Cys Glu Lys Cys Ala Lys Asp Cys Val Cys Lys
40                      45              50

Gly Gly Glu Ala Ala Glu Ala Glu Ala Glu Lys Cys Ser
            55              60                      65

Cys Cys Gln ( 2 ) INFORMATION FOR SEQ ID NO: 3:

( i ) SEQUENCE CHARACTERISTICS:
    ( A ) LENGTH: 26
    ( B ) TYPE: Amino Acid
    ( C ) STRANDEDNESS: Unknown
    ( D ) TOPOLOGY: Linear ( i i ) MOLECULE TYPE: Peptide ( x i ) SEQUENCE DESCRIPTION: SEQ ID NO:3:

Met Asp Pro Glu Thr Cys Pro Cys Pro Ser Gly Gly Ser
 1               5                       10

Cys Thr Cys Ala Asp Ser Cys Lys Cys Glu Gly Cys Lys
        15              20                  25